US010857317B2

(12) United States Patent
Costella et al.

(10) Patent No.: US 10,857,317 B2
(45) Date of Patent: Dec. 8, 2020

(54) HUFF COUGH SIMULATION DEVICE

(71) Applicant: TRUDELL MEDICAL INTERNATIONAL, London (CA)

(72) Inventors: Stephen Costella, London (CA); Robert Morton, London (CA); James Schmidt, London (CA)

(73) Assignee: Trudell Medical International, London (CA)

( * ) Notice: Subject to any disclaimer, the term of this patent is extended or adjusted under 35 U.S.C. 154(b) by 386 days.

(21) Appl. No.: 15/778,154

(22) PCT Filed: Dec. 2, 2016

(86) PCT No.: PCT/IB2016/057311
§ 371 (c)(1),
(2) Date: May 22, 2018

(87) PCT Pub. No.: WO2017/093966
PCT Pub. Date: Jun. 8, 2017

(65) Prior Publication Data
US 2018/0353715 A1 Dec. 13, 2018

Related U.S. Application Data

(60) Provisional application No. 62/263,263, filed on Dec. 4, 2015.

(51) Int. Cl.
*A61M 16/00* (2006.01)
*A61M 16/20* (2006.01)
(Continued)

(52) U.S. Cl.
CPC ...... *A61M 16/0006* (2014.02); *A61M 15/002* (2014.02); *A61M 15/0086* (2013.01);
(Continued)

(58) Field of Classification Search
CPC ............ A61M 16/0006; A61M 16/201; A61M 16/206; A61M 16/207; A61M 16/208;
(Continued)

(56) References Cited

U.S. PATENT DOCUMENTS

| 393,869 A | 12/1888 | Warren |
| 938,808 A | 11/1909 | Yount |

(Continued)

FOREIGN PATENT DOCUMENTS

| EP | 0 372 148 A1 | 6/1990 |
| EP | 0 678 306 A2 | 10/1995 |

(Continued)

OTHER PUBLICATIONS

International Search Report for PCT/IB2016/057311 (4 pgs).
(Continued)

*Primary Examiner* — Bradley H Philips
*Assistant Examiner* — Vincent D Hoang
(74) *Attorney, Agent, or Firm* — Brinks Gilson & Lione

(57) ABSTRACT

A respiratory treatment device having an inlet configured to receive exhaled air into the device, an outlet configured to permit exhaled air to exit the device, a valve moveable in response to a threshold exhalation pressure at the inlet between a closed position where the flow of air from the inlet to the outlet is restricted, and an open exhalation position where the flow of air from the inlet to the outlet is less restricted, and a valve brace configured to support the valve, wherein a position of the valve brace relative to the valve is selectively adjustable to increase or decrease the threshold exhalation pressure.

16 Claims, 15 Drawing Sheets

(51) Int. Cl.
*A61M 16/08* (2006.01)
*A61M 15/00* (2006.01)
*A61M 16/14* (2006.01)
*A61M 39/24* (2006.01)
*A63B 23/18* (2006.01)

(52) U.S. Cl.
CPC .... *A61M 16/0808* (2013.01); *A61M 16/0866* (2014.02); *A61M 16/14* (2013.01); *A61M 16/201* (2014.02); *A61M 16/208* (2013.01); *A61M 39/24* (2013.01); *A63B 23/18* (2013.01); *A61M 15/009* (2013.01); *A61M 15/0021* (2014.02); *A61M 2039/244* (2013.01); *A61M 2202/064* (2013.01); *A61M 2205/05* (2013.01)

(58) Field of Classification Search
CPC .......... A61M 16/209; A61M 2039/244; A63B 23/18
USPC .......................................................... 482/13
See application file for complete search history.

(56) References Cited

U.S. PATENT DOCUMENTS

| | | | |
|---|---|---|---|
| 2,670,739 A | 3/1954 | NcNeill | |
| 2,918,917 A | 12/1959 | Emerson | |
| 3,486,502 A | 12/1969 | Wilson | |
| 3,710,780 A | 1/1973 | Milch | |
| 3,908,987 A | 9/1975 | Boehringer | |
| 4,054,134 A * | 10/1977 | Kritzer | A61M 16/00 128/205.24 |
| 4,062,358 A | 12/1977 | Kritzer | |
| 4,182,366 A | 1/1980 | Boehringer | |
| 4,198,969 A | 4/1980 | Virag | |
| 4,210,174 A | 7/1980 | Eross | |
| 4,221,381 A | 9/1980 | Ericson | |
| 4,226,233 A | 10/1980 | Kritzer | |
| 4,231,375 A | 11/1980 | Boehringer et al. | |
| 4,267,832 A | 5/1981 | Hakkinen | |
| 4,275,722 A | 6/1981 | Sorensen | |
| 4,298,023 A | 11/1981 | McGinnis | |
| 4,327,740 A | 5/1982 | Shuman | |
| 4,403,616 A | 9/1983 | King | |
| 4,436,090 A | 3/1984 | Darling | |
| 4,470,412 A | 9/1984 | Nowacki et al. | |
| 4,473,082 A | 9/1984 | Gereg | |
| 4,487,207 A | 12/1984 | Fitz | |
| 4,533,137 A | 8/1985 | Sonne | |
| 4,601,465 A | 7/1986 | Roy | |
| 4,611,591 A | 9/1986 | Inui et al. | |
| 4,635,631 A | 1/1987 | Izumi | |
| 4,651,731 A | 3/1987 | Vicenzi et al. | |
| 4,739,987 A | 4/1988 | Nicholson | |
| 4,770,413 A * | 9/1988 | Green | A63B 23/18 137/269.5 |
| 4,854,574 A | 8/1989 | Larson | |
| 4,951,661 A | 8/1990 | Sladek | |
| 4,973,047 A | 11/1990 | Norell | |
| 4,981,295 A | 1/1991 | Belman et al. | |
| 5,018,517 A | 5/1991 | Liardet | |
| 5,042,467 A | 8/1991 | Foley | |
| 5,065,746 A | 11/1991 | Steen | |
| 5,190,036 A | 3/1993 | Linder | |
| 5,193,529 A | 3/1993 | Labaere | |
| 5,253,651 A * | 10/1993 | Stockwell | G01F 1/28 482/13 |
| 5,345,930 A | 9/1994 | Cardinal et al. | |
| 5,381,789 A | 1/1995 | Marquardt | |
| 5,397,337 A | 3/1995 | Jaeger et al. | |
| 5,451,190 A | 9/1995 | Liardet | |
| 5,479,920 A | 1/1996 | Piper et al. | |
| 5,518,002 A | 5/1996 | Wolf et al. | |
| 5,540,220 A | 7/1996 | Gropper et al. | |
| 5,569,122 A | 10/1996 | Cegla | |
| 5,570,682 A | 11/1996 | Johnson | |
| 5,598,839 A | 2/1997 | Niles et al. | |
| 5,613,489 A | 3/1997 | Miller | |
| 5,645,049 A | 7/1997 | Foley et al. | |
| 5,647,345 A | 7/1997 | Saul | |
| 5,655,520 A | 8/1997 | Howe | |
| 5,658,221 A | 8/1997 | Hougen | |
| 5,791,339 A | 8/1998 | Winter | |
| 5,829,429 A | 11/1998 | Hughes | |
| 5,848,588 A | 12/1998 | Foley et al. | |
| 5,857,957 A | 1/1999 | Lin | |
| 5,862,802 A | 1/1999 | Bird | |
| 5,890,998 A | 4/1999 | Hougen | |
| 5,893,361 A | 4/1999 | Hughes | |
| 5,896,857 A | 4/1999 | Hely | |
| 5,899,832 A | 5/1999 | Hougen | |
| 5,910,071 A | 6/1999 | Hougen | |
| 5,925,831 A | 7/1999 | Storsved | |
| 6,026,807 A | 2/2000 | Puderbaugh et al. | |
| 6,044,841 A | 4/2000 | Verdun et al. | |
| 6,058,932 A | 5/2000 | Hughes | |
| 6,066,101 A | 5/2000 | Johnson | |
| 6,067,984 A | 5/2000 | Piper | |
| 6,083,141 A | 7/2000 | Hougen | |
| 6,089,105 A | 7/2000 | Ricciardelli | |
| 6,102,038 A | 8/2000 | Devries | |
| 6,167,881 B1 | 1/2001 | Hughes | |
| 6,176,235 B1 | 1/2001 | Benarrouch et al. | |
| D440,651 S | 4/2001 | Foran | |
| 6,230,708 B1 * | 5/2001 | Radko | A61M 16/024 128/205.24 |
| 6,240,917 B1 | 6/2001 | Andrade | |
| 6,253,766 B1 | 7/2001 | Niles | |
| 6,293,279 B1 | 9/2001 | Schmidt et al. | |
| 6,340,025 B1 | 1/2002 | Van Brunt | |
| 6,345,617 B1 | 2/2002 | Engelbreth et al. | |
| 6,412,481 B1 | 7/2002 | Bienvenu et al. | |
| 6,500,095 B1 | 12/2002 | Hougen | |
| 6,539,938 B2 | 4/2003 | Weinstein et al. | |
| 6,557,549 B2 | 5/2003 | Schmidt et al. | |
| 6,581,595 B1 | 6/2003 | Murdock et al. | |
| 6,581,596 B1 | 6/2003 | Truitt | |
| 6,581,598 B1 | 6/2003 | Foran et al. | |
| 6,581,600 B2 | 6/2003 | Bird | |
| 6,595,203 B1 | 7/2003 | Bird | |
| 6,606,989 B1 | 8/2003 | Brand | |
| 6,615,831 B1 | 9/2003 | Truitt | |
| 6,631,721 B1 | 10/2003 | Salter et al. | |
| 6,659,100 B2 | 12/2003 | O'Rourke | |
| 6,702,769 B1 | 3/2004 | Fowler-Hawkins | |
| 6,708,690 B1 | 3/2004 | Hete et al. | |
| 6,708,691 B1 | 3/2004 | Hayek | |
| 6,726,598 B1 * | 4/2004 | Jarvis | A63B 23/18 128/200.24 |
| D490,519 S | 5/2004 | Pelerossi et al. | |
| 6,776,159 B2 | 8/2004 | Pelerossi et al. | |
| 6,848,443 B2 | 2/2005 | Schmidt et al. | |
| 6,851,425 B2 | 2/2005 | Jaffre | |
| 6,860,265 B1 | 3/2005 | Emerson | |
| 6,889,687 B1 | 5/2005 | Olsson | |
| 6,904,906 B2 | 6/2005 | Salter | |
| 6,923,181 B2 | 8/2005 | Tuck | |
| 6,929,007 B2 | 8/2005 | Emerson | |
| 6,984,214 B2 | 1/2006 | Fowler-Hawkins | |
| 7,059,324 B2 | 6/2006 | Pelerossi et al. | |
| 7,096,866 B2 | 8/2006 | Be'eri et al. | |
| 7,134,434 B2 | 11/2006 | Truitt et al. | |
| 7,165,547 B2 | 1/2007 | Truitt et al. | |
| 7,188,621 B2 | 3/2007 | DeVries | |
| 7,191,776 B2 | 3/2007 | Niles | |
| 7,191,780 B2 | 3/2007 | Faram | |
| 7,204,245 B2 * | 4/2007 | Johnson | A61M 15/0086 128/200.14 |
| 7,214,170 B2 | 5/2007 | Summers et al. | |
| 7,383,740 B2 | 6/2008 | Krasilchikov et al. | |
| 7,617,821 B2 | 11/2009 | Hughes | |
| 7,699,054 B2 | 4/2010 | Pelerossi et al. | |
| 7,717,847 B2 | 5/2010 | Smith | |

(56) References Cited

U.S. PATENT DOCUMENTS

| | | | |
|---|---|---|---|
| 7,771,472 B2 | 8/2010 | Hendricksen | |
| 7,779,841 B2 | 8/2010 | Dunsmore et al. | |
| 7,798,148 B2 | 9/2010 | Doshi | |
| 7,856,979 B2 | 12/2010 | Doshi | |
| 7,909,033 B2 | 3/2011 | Faram | |
| 7,927,293 B1 | 4/2011 | Ignagni et al. | |
| 8,006,922 B2 | 8/2011 | Katzer | |
| 8,025,051 B2 | 9/2011 | Dagsland | |
| 8,025,054 B2 | 9/2011 | Dunsmore et al. | |
| 8,043,236 B2 | 10/2011 | Goldshtein et al. | |
| 8,051,854 B2 | 11/2011 | Faram | |
| RE43,174 E | 2/2012 | Schmidt et al. | |
| 8,118,024 B2 | 2/2012 | Devries et al. | |
| 8,118,713 B2 | 2/2012 | Foley et al. | |
| 8,225,785 B2 | 7/2012 | Richards et al. | |
| 8,251,876 B2 | 8/2012 | Boerst et al. | |
| 8,327,849 B2 | 12/2012 | Grychowski et al. | |
| 8,460,223 B2 | 6/2013 | Huster et al. | |
| 8,469,029 B2 | 6/2013 | Brown et al. | |
| 8,485,179 B1 | 7/2013 | Meyer | |
| 8,528,547 B2 | 9/2013 | Dunsmore | |
| 8,539,951 B1 | 9/2013 | Meyer et al. | |
| 8,985,111 B2 | 3/2015 | Grychowski et al. | |
| D731,050 S | 6/2015 | Meyer | |
| 9,149,589 B2 | 10/2015 | Meyer et al. | |
| 9,220,855 B2 | 12/2015 | Meyer | |
| 9,517,315 B2 | 12/2016 | Meyer | |
| D776,804 S | 1/2017 | Meyer | |
| D778,429 S | 2/2017 | Engelbreth et al. | |
| D780,906 S | 3/2017 | Engelbreth et al. | |
| 9,636,473 B2 | 5/2017 | Meyer | |
| 9,737,677 B2 | 8/2017 | Grychowski et al. | |
| 9,808,588 B1 | 11/2017 | Meyer et al. | |
| 9,849,257 B2 | 12/2017 | Meyer et al. | |
| 2001/0052344 A1* | 12/2001 | Doshi | A61B 17/12036 128/207.16 |
| 2003/0036786 A1 | 2/2003 | Duren | |
| 2004/0016428 A9 | 1/2004 | Lurie | |
| 2005/0016533 A1 | 1/2005 | Schuller et al. | |
| 2006/0032607 A1 | 2/2006 | Wisniewski | |
| 2007/0259759 A1 | 11/2007 | Sumners et al. | |
| 2008/0053452 A1 | 3/2008 | Brown | |
| 2008/0053456 A1 | 3/2008 | Brown et al. | |
| 2008/0078383 A1 | 4/2008 | Richards | |
| 2008/0096728 A1 | 4/2008 | Foley | |
| 2009/0241949 A1 | 10/2009 | Smutney et al. | |
| 2010/0101573 A1 | 4/2010 | Foley | |
| 2010/0139655 A1 | 6/2010 | Genosar | |
| 2010/0282253 A1 | 11/2010 | Newman, Jr. | |
| 2010/0307487 A1 | 12/2010 | Dunsmore et al. | |
| 2011/0124470 A1 | 5/2011 | Spurling et al. | |
| 2011/0290240 A1 | 12/2011 | Meyer et al. | |
| 2012/0097164 A1 | 4/2012 | Rozario et al. | |
| 2012/0285460 A1 | 11/2012 | Smith et al. | |
| 2012/0304988 A1 | 12/2012 | Meyer | |
| 2013/0118498 A1 | 5/2013 | Robitaille | |
| 2013/0133649 A1 | 5/2013 | Grychowski et al. | |
| 2013/0184619 A1 | 7/2013 | Von Hollen et al. | |
| 2013/0220325 A1 | 8/2013 | Davis | |
| 2013/0284171 A1 | 10/2013 | Adam et al. | |
| 2013/0312746 A1 | 11/2013 | Grychowski | |
| 2014/0041657 A1 | 2/2014 | Meyer | |
| 2014/0150790 A1 | 6/2014 | Meyer et al. | |
| 2015/0013671 A1* | 1/2015 | Costella | A61M 15/0086 128/200.23 |
| 2015/0053209 A1 | 2/2015 | Meyer et al. | |
| 2015/0151060 A1 | 2/2015 | Grychowski et al. | |
| 2015/0224269 A1 | 8/2015 | Alizoti et al. | |
| 2015/0297848 A1 | 10/2015 | Meyer et al. | |
| 2015/0374939 A1 | 12/2015 | Meyer et al. | |
| 2016/0136369 A1 | 5/2016 | Meyer et al. | |
| 2016/0310695 A1 | 10/2016 | Meyer et al. | |
| 2017/0028161 A1 | 2/2017 | Meyer et al. | |
| 2017/0049979 A1 | 2/2017 | Meyer et al. | |
| 2017/1028683 | 5/2017 | Meyer et al. | |
| 2017/0312461 A1 | 11/2017 | Grychowski et al. | |
| 2017/0333661 A1* | 11/2017 | Bennett | A61M 16/0006 |

FOREIGN PATENT DOCUMENTS

| | | |
|---|---|---|
| EP | 1 464 357 A1 | 10/2004 |
| EP | 1 435 251 B1 | 6/2006 |
| EP | 1 103 287 B1 | 6/2007 |
| EP | 1 897 576 A1 | 3/2008 |
| EP | 1 908 489 A1 | 4/2008 |
| EP | 2444114 A1 | 4/2012 |
| EP | 2455137 A2 | 5/2012 |
| GB | 2 425 488 A | 11/2006 |
| WO | WO 1989/03707 A1 | 5/1989 |
| WO | WO 1996/40376 A1 | 12/1996 |
| WO | WO 1999/16490 A1 | 4/1999 |
| WO | WO 2000/27455 A1 | 5/2000 |
| WO | WO 01/89618 A1 | 11/2001 |
| WO | WO 2007/061648 A3 | 5/2007 |
| WO | WO 2007/119104 A3 | 10/2007 |
| WO | WO 2008/063966 A1 | 5/2008 |
| WO | WO 2008/122045 A1 | 10/2008 |
| WO | WO 2009/131965 | 10/2009 |
| WO | WO 2011/010279 A1 | 1/2011 |
| WO | WO 2011/058470 | 5/2011 |
| WO | WO 2012/038864 A2 | 3/2012 |
| WO | WO 2012/042255 A1 | 4/2012 |
| WO | WO 2013/001398 A1 | 1/2013 |
| WO | WO 2014/202923 | 12/2014 |
| WO | WO 2014/202924 | 12/2014 |
| WO | WO 2014/203115 | 12/2014 |
| WO | WO 2015/003249 | 1/2015 |
| WO | WO 2016/012740 | 1/2016 |

OTHER PUBLICATIONS

Written Opinion of the International Searching Authority for International Application No. PCT/IB2016/057311 dated Mar. 3, 2017.
International Preliminary Report on Patentability for International Application No. PCT/IB2016/057311 dated Jun. 5, 2018.
U.S. Appl. No. 15/453,767, filed Mar. 8, 2017, Meyer et al.
Web page entitled Bronchial Hygiene, acapella Vibratory PEP Therapy System accessed from http://www.smiths-medical.com/catalog/bronchial-hygiene/acapella/acapella.html on Jul. 7, 2009.
Web page entitled Thayer Quake accessed from http://www.thayermedical.com/quake.htm on Jul. 7, 2009.
Human growth hormone, cortisol, and acid-base balance changes after hyperventilation and breath-holding; PubMed—indexed for MEDLINE; Int J Sports Med., Dec. 1986; 7(6):311-5, Djarova T.
Bosco C, Cardinale M. & Tsarpela O (1999). Influence of vibration on mechanical power and electromyogram activity in human arm flexor muscles. Eur J Appl Physiol 79, 306-311.
David Sumners; Power Breathing and Strength; http://EzineArticles.com/972576 Published: Feb. 7, 2008.
Good Vibrations blog; http://vibrotraining.blogspot.com, Earliest posting Jan. 17, 2008.
Breathtaking News; More Youbreathe; Aug. 10, 2007.
PCT International Search Report for PCT/IB2012/001089, dated Oct. 5, 2012.
PCT International Written Opinion for PCT/IB2012/001089, dated Oct. 5, 2012.
PCT International Search Report for PCT/CA2014/000562 dated Oct. 16, 2014.
PCT Written Opinion for PCT/CA2014/000562 dated Oct. 16, 2014.
Supplemental European Search Report for related application No. 14822301.9; dated Feb. 21, 2017 (8 pgs).

* cited by examiner

HUFF COUGH SIMULATION DEVICE

RELATED APPLICATION

This application claims the benefit of U.S. Provisional Application No. 62/263,263, filed on Dec. 4, 2015, which is incorporated herein by reference.

TECHNICAL FIELD

The present disclosure relates to a respiratory treatment device, and in particular, to a Huff Cough simulation device.

BACKGROUND

The Huff Cough is an effective technique for clearance of pulmonary secretions from the airways. It is often utilized in the treatment of COPD, or Chronic Obstructive Pulmonary Disease, although it may also be useful in other respiratory treatments. In general, the Huff Cough involves a patient using his or her diaphragm to breathe in slowly, holding the breath for two to three seconds, and forcing the breath out of his or her mouth in one quick burst of air, making sure the back of the throat is kept open. This technique is typically repeated multiple times during a single treatment. The length and force of the breath may be varied in order to treat different portions of a patient's airways.

Despite its efficacy, the Huff Cough may be difficult for some populations to effectively perform, requiring coaching from respiratory professionals. To that end, a user-friendly Huff Cough simulation device that provides physicians and patients with improved control over the treatment is desirable.

BRIEF SUMMARY

In one aspect, a respiratory treatment device includes an inlet configured to receive exhaled air into the device, an outlet configured to permit exhaled air to exit the device, a valve moveable in response to a threshold exhalation pressure at the inlet between a closed position where the flow of air from the inlet to the outlet is restricted, and an open exhalation position where the flow of air from the inlet to the outlet is less restricted, and a valve brace configured to support the valve.

In another aspect, a respiratory treatment device may include an inlet configured to receive exhaled air into the device, an outlet configured to permit exhaled air to exit the device, an opening positioned between the inlet and the outlet, a valve moveable in response to a threshold exhalation pressure at the inlet between a closed position where the flow of air through the opening is restricted, and an open exhalation position where the flow of air through the opening is less restricted, and a valve seat surrounding the opening configured to retain the valve in the closed position until a threshold exhalation pressure is obtained at the inlet.

In another aspect, A respiratory treatment device includes an inlet configured to receive exhaled air into the device, an outlet configured to permit exhaled air to exit the device, a valve moveable in response to a threshold exhalation pressure at the inlet between a closed position where the flow of air from the inlet to the outlet is restricted, and an open exhalation position where the flow of air from the inlet to the outlet is less restricted, and a reset button configured to return the valve from the open exhalation position to the closed position.

In another aspect, a position of the valve brace relative to the valve is selectively adjustable to increase or decrease the threshold exhalation pressure. Selective adjustment of the position of the valve brace relative to the valve increases or decrease a stiffness of the valve. Selective adjustment of the position of the valve brace relative to the valve also increases or decreases an area of the valve supported by the valve brace.

In another aspect, a valve seat may be configured to retain the valve in the closed position until a threshold exhalation pressure is obtained at the inlet. The valve seat may be positioned to engage a periphery of the valve.

In another aspect, a reset button may be configured to return the valve from the open exhalation position to the closed position. The resent button may be connected to the device by a molded-in spring. The reset button may be selectively rotatable to adjust the position of the valve brace relative to the valve. The reset button may include a plurality of gear teeth configured to engage a plurality of teeth on the valve brace.

In another aspect, the valve may be a flap valve, for example, a two-way flap valve. The valve may be biased toward the closed position.

In another aspect, a first housing component and a second housing component may be removably connected. The inlet may include a mucus trap. The mucus trap may be removably connected to one of the first housing component or the second housing component. The inlet may include a screen having a plurality of openings.

In another aspect, the valve may be moveable in response to an inhalation pressure at the inlet between the closed between and an open inhalation position where the flow of air from the outlet to the inlet is less restricted.

DETAILED DESCRIPTION

Described herein is an embodiment of a respiratory treatment device that replicates or simulates a Huff Cough. In general, this treatment device prevents the flow of exhaled air through the device until a threshold pressure is reached at a user interface. Once a threshold pressure is reached, the device releases the exhaled air, causing a rapid increase in the flow of exhaled air through the device. This sharp increase in airflow translates directly to high air velocities in the user's airways, and therefore higher shear forces on secretions lining the airways, similar to that experienced during a Huff Cough. Other Huff Cough simulation devices are shown and described in U.S. patent application Ser. No. 14/329,011, filed on Jul. 11, 2014, pending, which is hereby incorporated by reference in its entirety.

The embodiment described herein is notable in that the threshold pressure at which exhaled air is released is selectively adjustable. This embodiment is also notable in that the release of exhaled air at a threshold pressure is dependent on a user's exhalation and easily repeatable by a user without coaching or supervision from a respiratory professional. Moreover, this embodiment is notable in that it does not include any metallic components (e.g., magnets, springs, etc.), which tend to increase production costs, and may be susceptible to corrosion.

Figure 1:
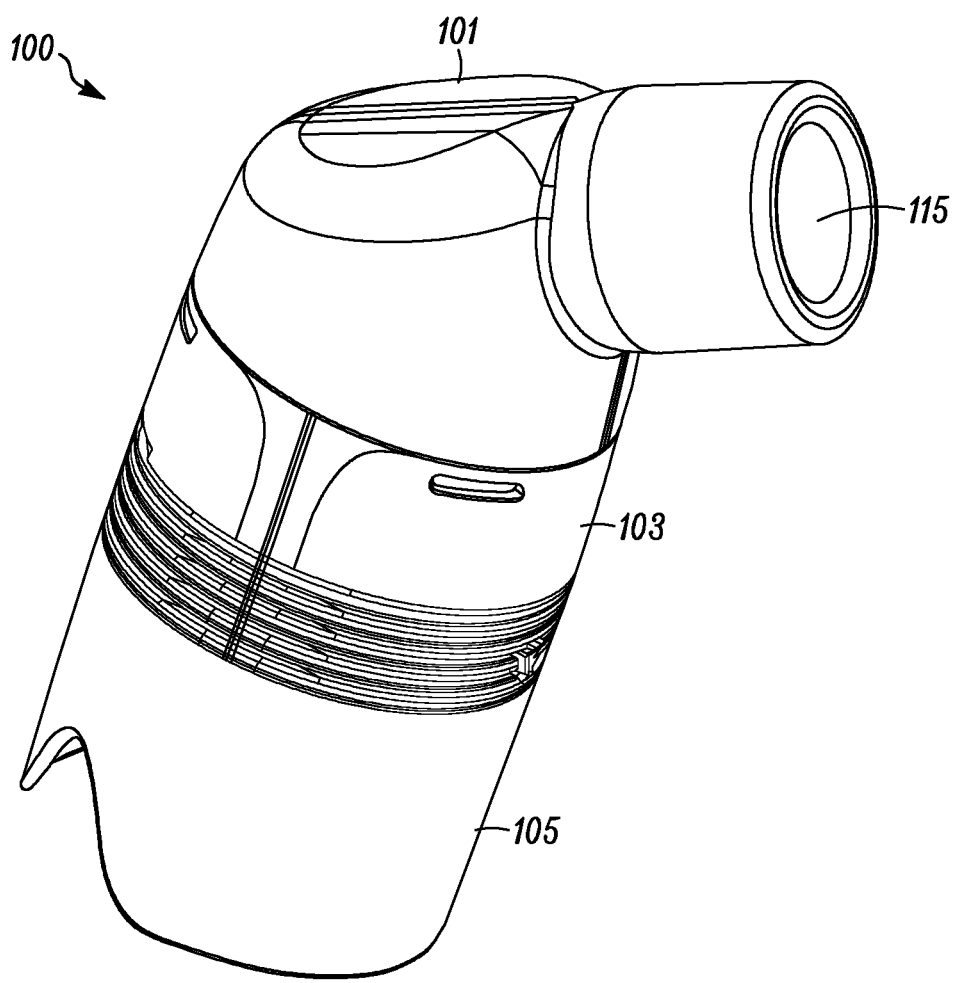
FIG. 1 is a perspective view of a Huff Cough simulation device.
Figure 2:
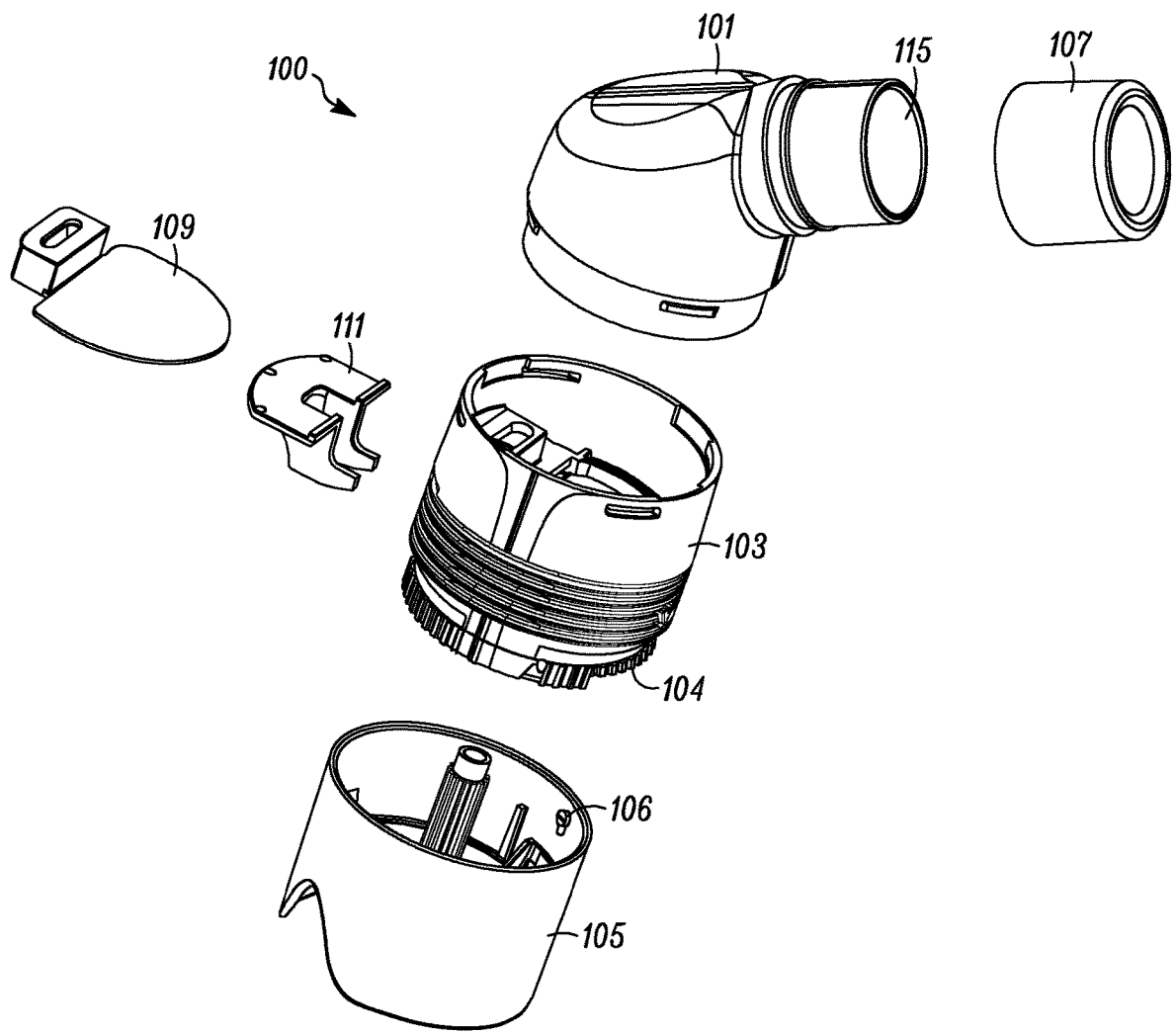
FIG. 2 is an exploded view of the device of FIG. 1.
Figure 3:
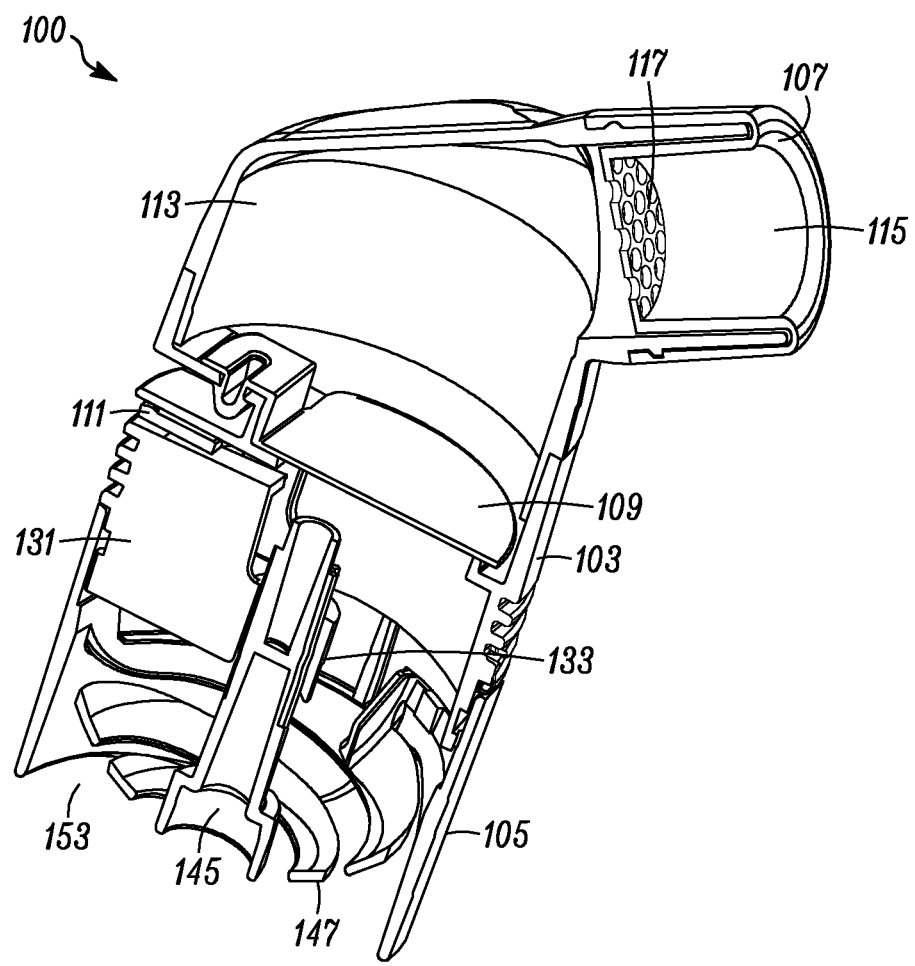
FIG. 3 is a cross-sectional perspective view of the device of FIG. 1.

FIGS. 1-3 show a Huff Cough simulation device 100. FIG. 1 is a perspective view of the device 100. FIG. 2. Is an exploded view of the device 100. FIG. 3 is a cross-sectional view of the device 100. In general, the device 100 includes a top housing portion 101, a middle housing portion 103, a bottom housing portion 105, a mucus trap 107, a valve 109, and a valve brace 111.

As seen in FIGS. 1-3, the top housing portion 101, the middle housing portion 103, and the bottom housing portion 105 are removably connectable such that the components of the device 100 may be periodically accessed for cleaning and/or replacement. The housing portions may be removably connectable by any suitable means, including for example, threading, compression fit, or snap fit. When connected, the top housing portion 101 and the middle housing portion 103 form an interior chamber 113.

Figure 4:
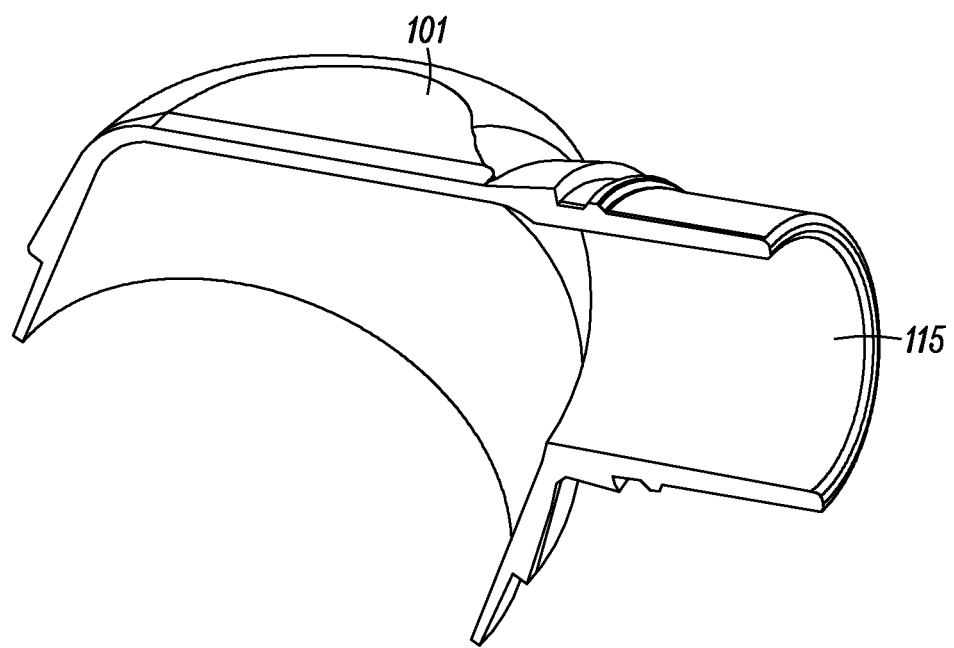
FIG. 4 is a cross-sectional perspective view of a top portion of the housing of the device of FIG. 1.

FIG. 4 is a cross-sectional view of the top housing portion 101. The top housing portion may be made of any suitable plastic material, including for example, a high-temperature polypropylene (PP). The top housing portion 101 includes an inlet or mouthpiece 115 for receiving exhaled air from a user. Preferably, the mouthpiece is circular and roughly 1 inch in diameter in order to promote glottal patency throughout a user's exhalation. However, it should be appreciated that other user interfaces may form, or may be in fluid communication with the inlet or mouthpiece 115, including for example, gas masks, breathing tubes, or the like. Moreover, it should be appreciated that the device 100 may be used in conjunction or combination with other respiratory treatment devices that administer therapy upon inhalation, including for example, a nebulizer, a metered dose inhaler with a valved holding chamber, or a dry powder inhaler. In this way, the device 100 may administer therapy upon a user's exhalation, while the aforementioned devices may administer therapy upon a user's inhalation.

Figure 5:
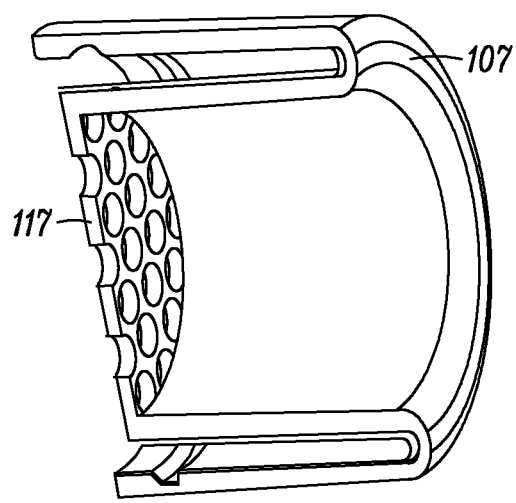
FIG. 5 is a cross-sectional perspective view of a mucus trap of the device of FIG. 1.

FIG. 5 is a cross-sectional view of the mucus trap 107. The mucus trap 107 may also be made of any suitable plastic material, such as a high-temperature polypropylene (PP). The mucus trap 107 is sized and shaped to fit around and within the mouthpiece 115, as shown in FIG. 3. The mucus trap 107 and the mouthpiece 115 may be removably connectable by any suitable means, including for example, snap fit (as shown in FIG. 3), compression fit, or threading. The mucus trap 107 includes a grate 117 having plurality of small openings, and is configured to capture any secretions expelled out of a user's mouth during exhalation, while permitting exhaled air to pass through the grate into the device 100.

Figure 6:
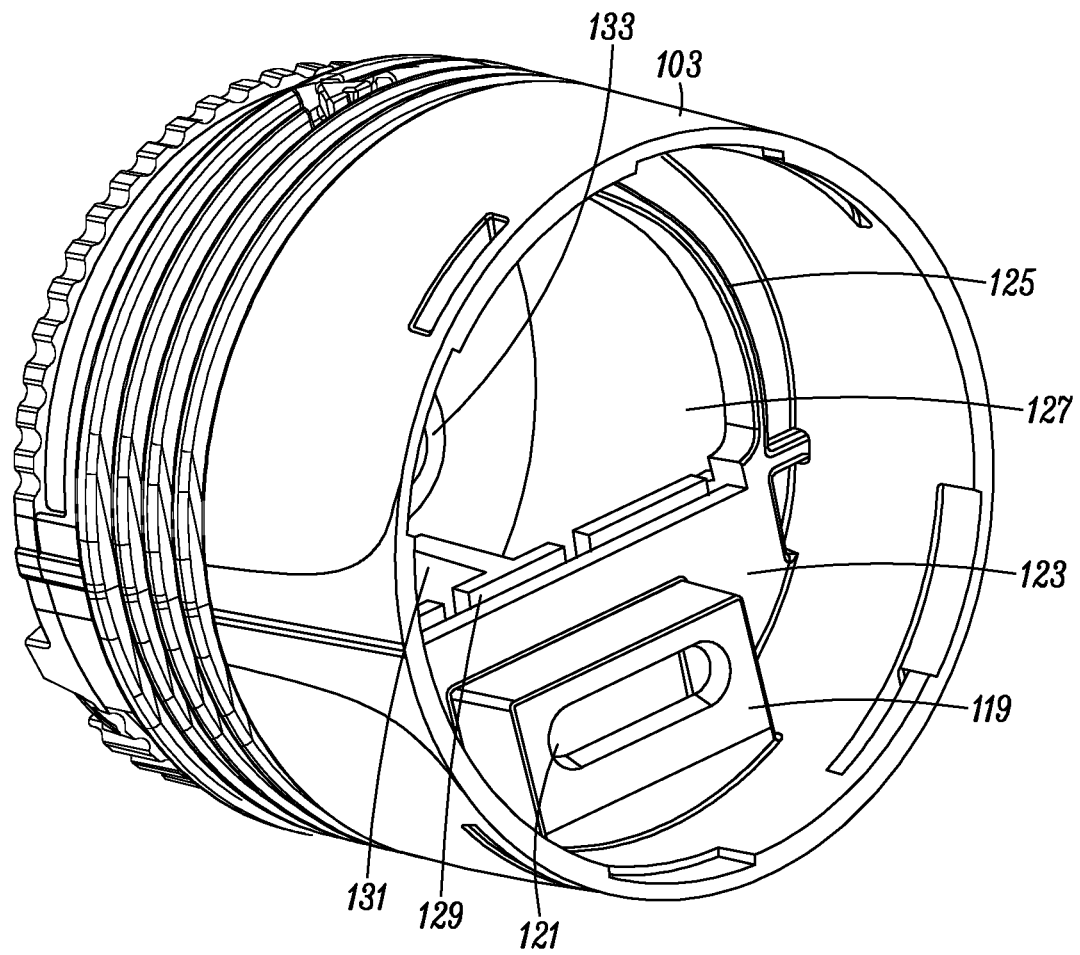
FIG. 6 is a perspective view of a middle portion of the housing of the device of FIG. 1.
Figure 7:
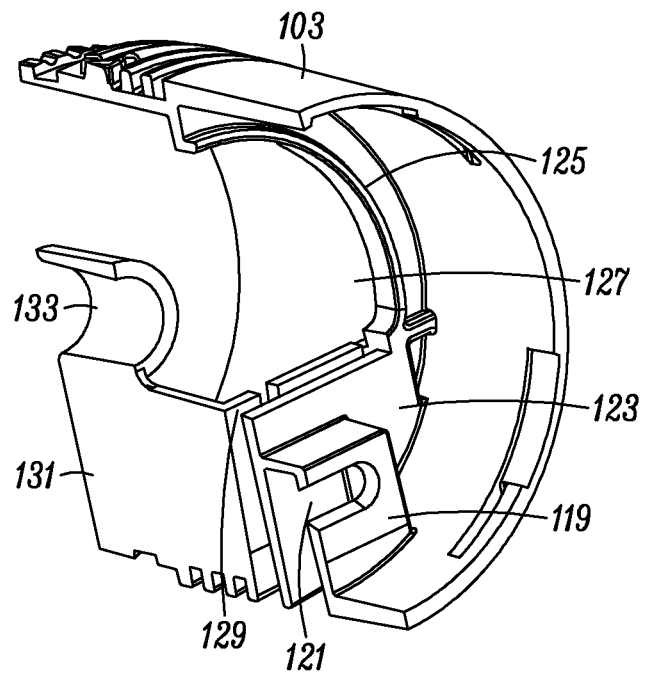
FIG. 7 is a cross-sectional perspective view of the middle portion of the housing of FIG. 6.

FIGS. 6-7 are perspective and cross-sectional views of the middle housing portion 103. The middle housing portion 103 may also be made of a suitable plastic material, such as high-temperature polypropylene (PP). The middle housing portion 103 includes a mount 119 having an opening 121 for receiving a barb 139 molded with the valve 109, a ledge 123 extending into the interior of the middle housing portion 103, and a rim 125 formed around the periphery of the middle housing portion 103. Together, the ledge 123 and the rim 125 form a valve seat for the valve 109 and define an opening 127 through which exhaled air passes through the middle housing portion 103 when the valve 109 is in an open position, as discussed below. The middle housing portion 103 also includes a slot 129 for receiving the valve brace 111, and a support structure 131 extending into the interior of the middle housing portion 103, having a cylindrical support 133 adapted to receive a rod extending from the reset button, as discussed below.

Figure 8:
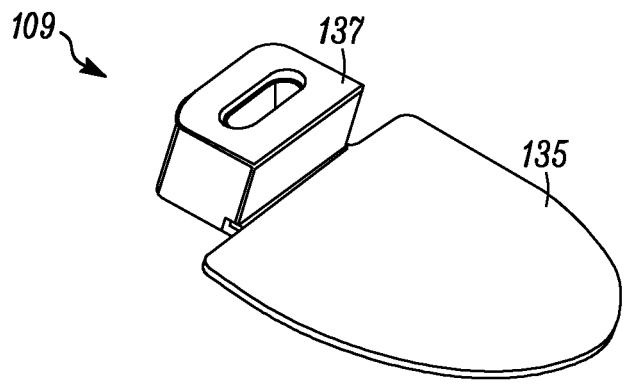
FIG. 8 is a perspective view of the valve of the device of FIG. 1.
Figure 9:
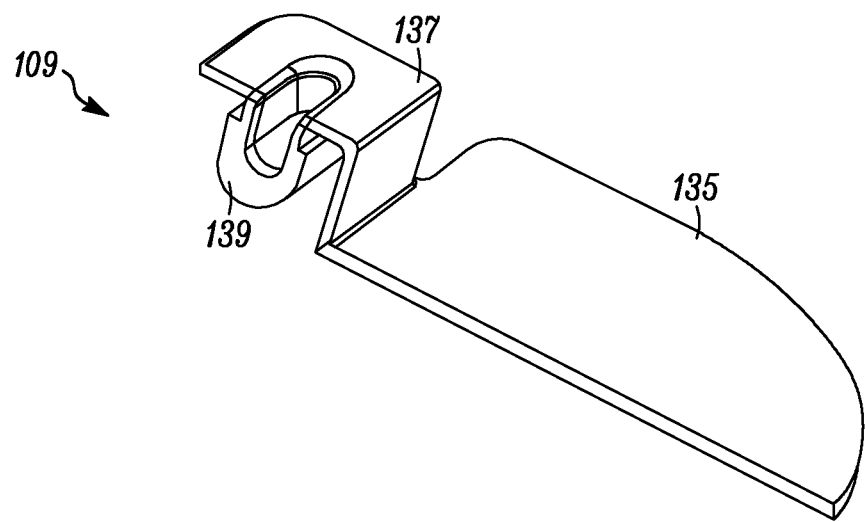
FIG. 9 is a cross-sectional perspective view of the valve of FIG. 8.

FIGS. 8-9 are perspective and cross-sectional views of the valve 109. In general, the valve 109 is configured as a flap valve having a flap 135 and a post 137 that includes a barb 139 for securing the valve 109 to the mount 119 in the middle housing portion 103. It should be appreciated that other means of securing the valve 109 to the middle housing portion 103 may be used, including for example, heat staking, living hinges, and other barb designs. The flap 135 is sized to cover the opening 121 and rest on the valve seat formed by the ledge 123 and rim 125 in the middle housing portion 103. The flap 135 is configured to bend relative to the post 137 between an open position (shown in FIG. 14) in a first direction, and during a valve reset, in the opposite direction (shown in FIG. 15). The flap 135 is also configured to open in the opposite direction toward an open inhalation position (e.g., as shown in FIG. 15) during a period of inhalation, or in response to an inhalation pressure at the inlet or mouthpiece 115. The valve may be made of a rubber material, for example, a silicone rubber, having a hardness of 40-50 Shore A durometer.

Figure 13:
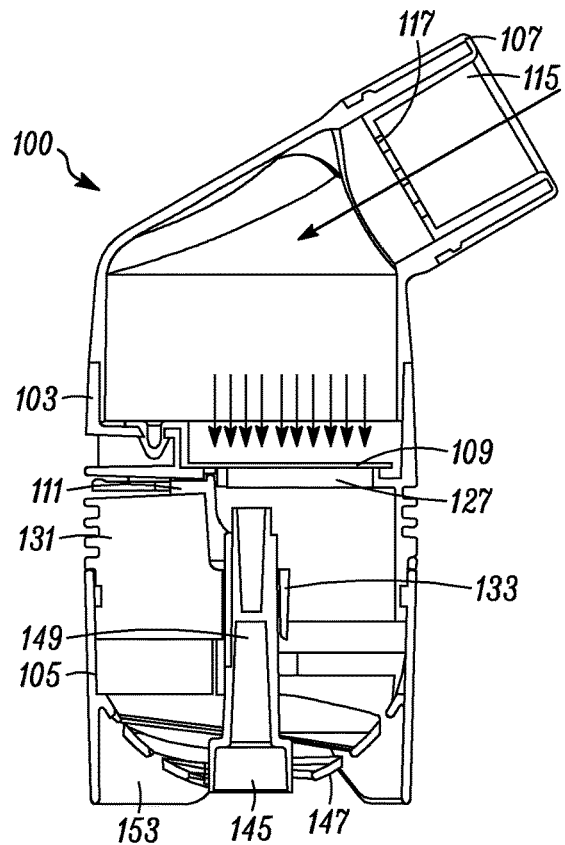
FIG. 13 is a cross-sectional view of the device of FIG. 1 during a period of exhalation, showing the valve of FIG. 8 in a closed position.
Figure 14:
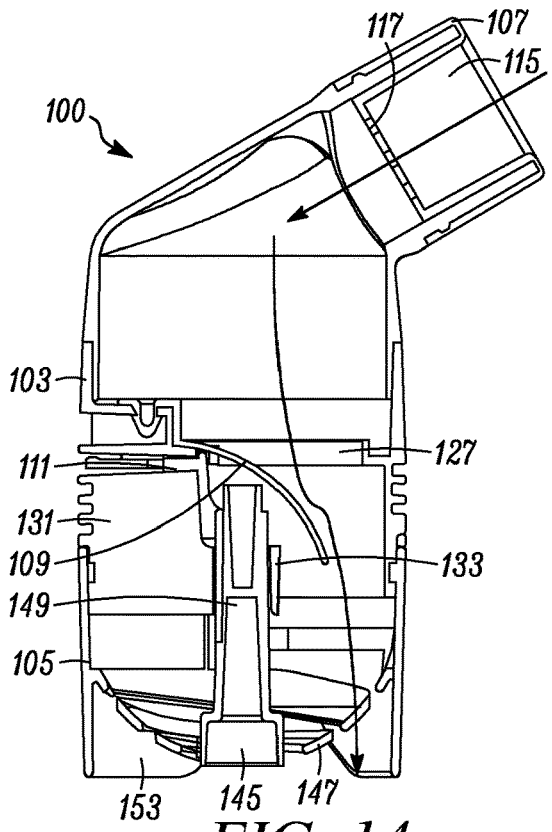
FIG. 14 is a cross-sectional view of the device of FIG. 1 during a period of exhalation, showing the valve of FIG. 8 in an open position.
Figure 15:
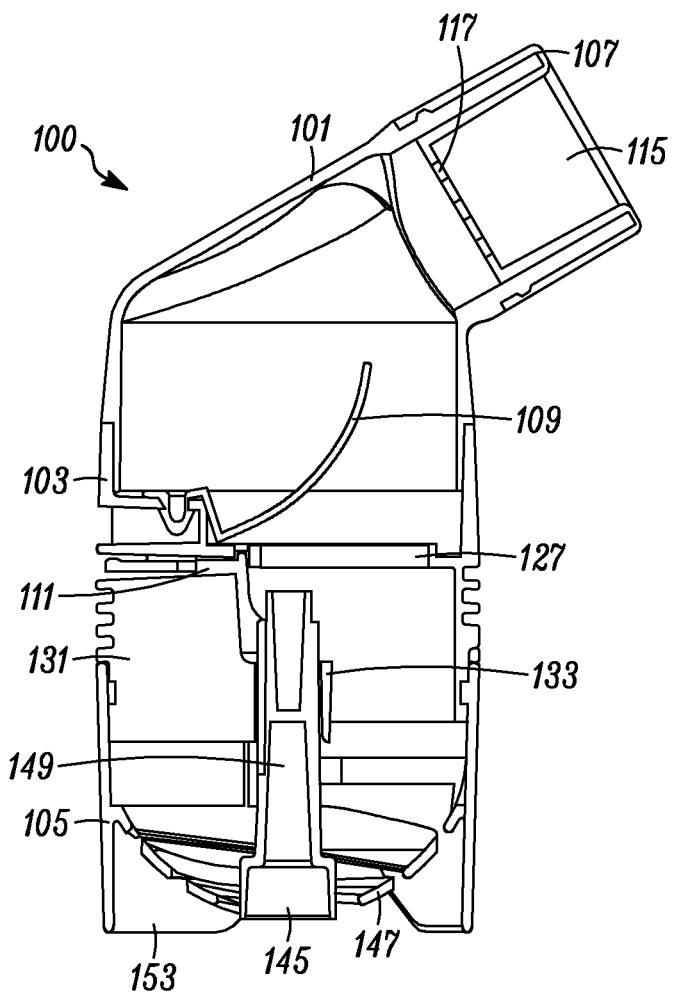
FIG. 15 is a cross-sectional view of the device of FIG. 1 after a period of exhalation, showing the valve of FIG. 8 being reset to the closed position shown in FIG. 13.

The interaction of the valve 109 with the valve seat formed by the ledge 123 and the rim 125 affects the threshold pressure at which the valve will blow through the opening 121, and move from the closed position, shown in FIG. 13, to an open position, shown in FIG. 14. For example, the diameter of the flap 135, the diameter of the opening 121, the stiffness or hardness of the valve material, the valve thickness, and the friction between the valve and valve seat and/or the valve brace 111, all affect the threshold pressure at which the valve will blow through the opening 121. The valve 109 may be accessed and selectively replaced with a valve having different properties in order to increase or decrease the threshold pressure.

Figure 10:
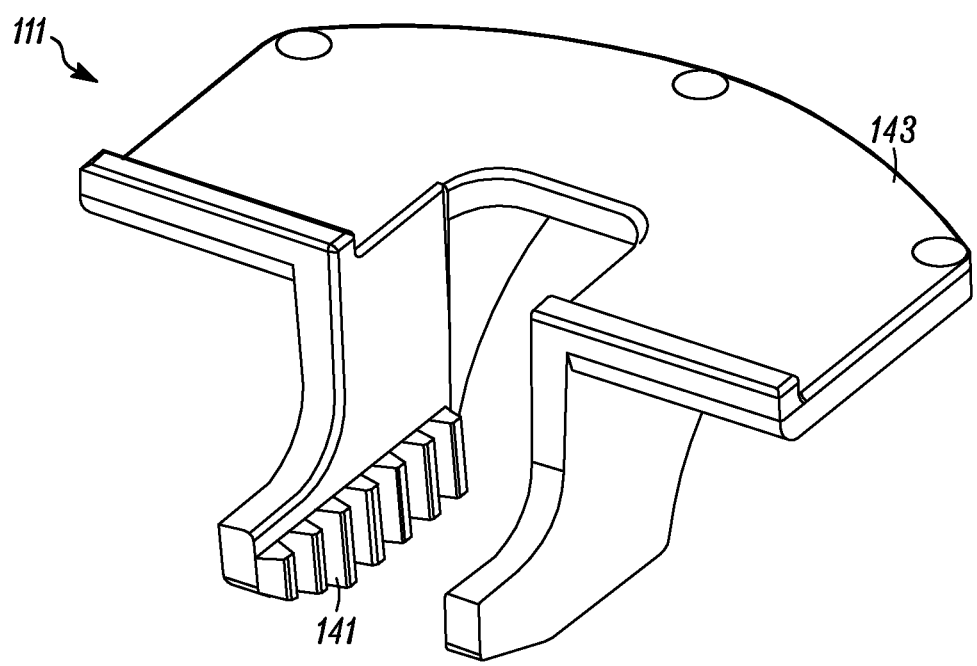
FIG. 10 is a perspective view of a valve brace of the device of FIG. 1.

FIG. 10 is a perspective view of the valve brace 111. The valve brace 111 is sized and shaped to fit in a sliding engagement within the slot 129 formed in the middle housing portion 103. The valve brace 111 further includes a support face 143 and series or a rack of teeth 141 extending therefrom configured to engage a corresponding series of gear teeth 151 (e.g., a pinion) on the lower housing portion 105. The valve brace 111 may also be made of a suitable plastic material, such as Acetal (POM) or poly (p-phylene oxide) (PPO).

Figure 11:
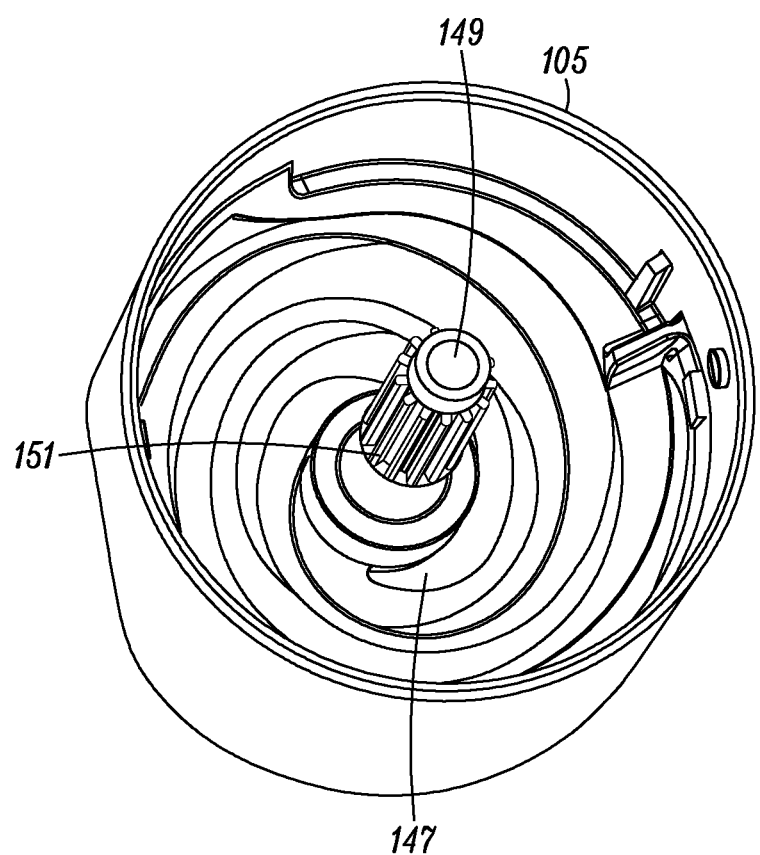
FIG. 11 is a perspective view of a lower portion of the housing of the device of FIG. 1, showing a reset button connected to the lower portion of the housing via a molded-in spring.
Figure 12:
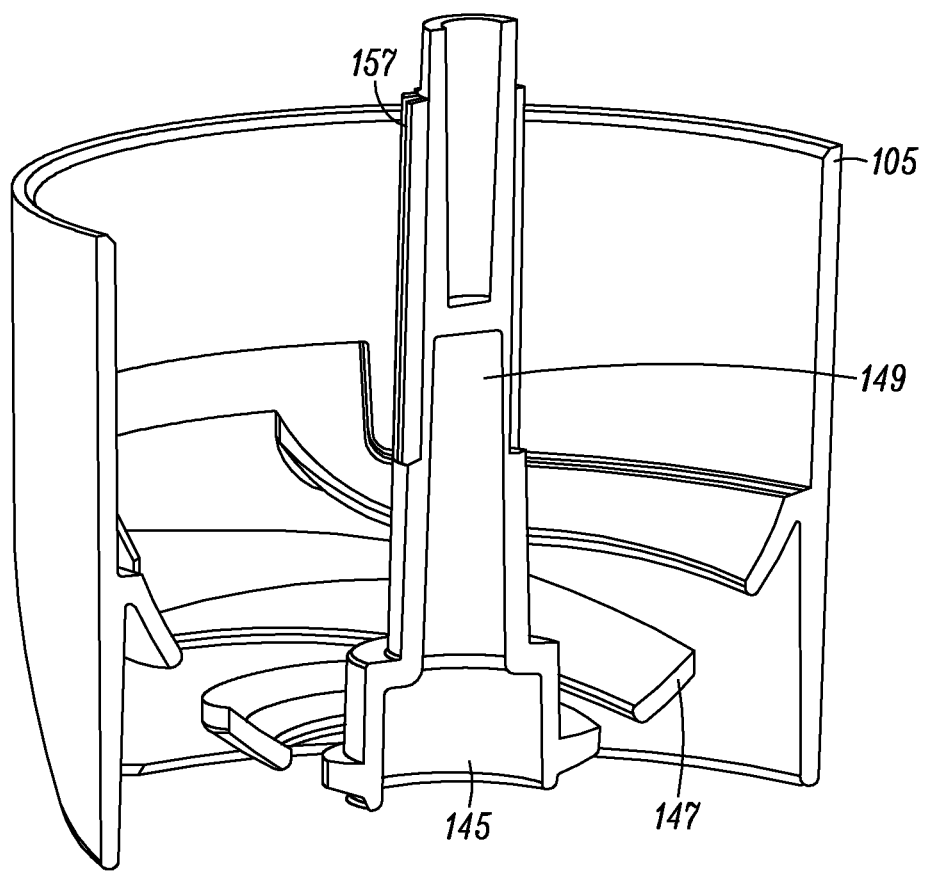
FIG. 12 is a cross-sectional perspective view of the lower portion of the housing of FIG. 11, showing the reset button connected to the lower portion via the molded-in spring.

FIGS. 11-12 are perspective and cross-sectional views of the lower housing portion 105. The lower housing portion 105 may also be made of a suitable plastic material, such as Acetal (POM). The lower housing portion 105 includes a reset button 145 connected to the lower housing portion 105 via a molded-in spring 147 comprised of a plurality of spiraling segments extending between the lower housing portion 105 and the reset button 145. An open end of the lower housing portion 105 functions as an outlet 153. Exhaled air is permitted to exit the device 100 through the openings formed between the spiraling segments of the molded-in spring 147, and ultimately, the outlet 153.

The reset button 145 further includes a rod 149 extending into the lower housing portion 105 that has a series of gear teeth 151 (e.g., a pinion) for engaging a corresponding series or a rack of teeth 141 on the valve brace 111. The reset button 145 may also include additional protrusions, wings, or markings (not shown) to aid a user in depressing and/or rotating the reset button 145. The molded-in spring 147 is configured to permit a user to push the reset button 145 and move the reset button 145 and rod 149 relative to the lower hosing portion 105 to reset the valve 109 to the closed position, as described further below. The series of gear teeth 151 on the rod 149 is configured to engage the rack of teeth 141 on the valve brace 111 such that rotation of the reset button 145 advances or retracts the valve brace 111 relative to the valve 109, as described further below.

Operation of the device 100 will now be described. FIGS. 13-15 are cross-sectional side views illustrating simulation of a Huff cough during a period of exhalation, and reset of the valve 109. FIGS. 16A-B and 17A-B are side and perspective views of the lower portion of the housing 105, illustrating operation of the reset button 145 and the molded-in spring 147 to reset the valve 109.

Operation of the device 100 begins with the valve 109 in a closed position, as shown in FIG. 13, where the flow of air through the opening 127 is restricted. As a user begins to exhale into the device 100 through the inlet or mouthpiece 115, exhalation pressure begins to build within the device 100, and specifically, against the valve 109. As exhalation pressure builds, the flap 135 on the valve 109 begins to deform into a bowl shape, bringing the periphery of the flap 135 closer to the edges of the valve seat formed by the ledge 123 and the rim 125 that define the opening 127. As the exhalation pressure continues to build, the periphery of the flap 135 continues to move closer to the edges of the valve seat. When a threshold exhalation pressure is achieved, the periphery of the flap 135 is no longer supported by the valve seat, and the flap 135 is free to quickly blow through the opening 127, as shown in FIG. 14, thereby resulting in a rapid flow of air through the device 100, from the mouthpiece 115 to the outlet 153. The rapid flow of air through the device 100 also results in high air flow velocities in the user's airways. In the event that secretions are loosened within the user's respiratory system and expelled out of the user's mouth, the mucus trap 107 may capture the discharge and prevent it from entering the device 100.

Figure 16A:
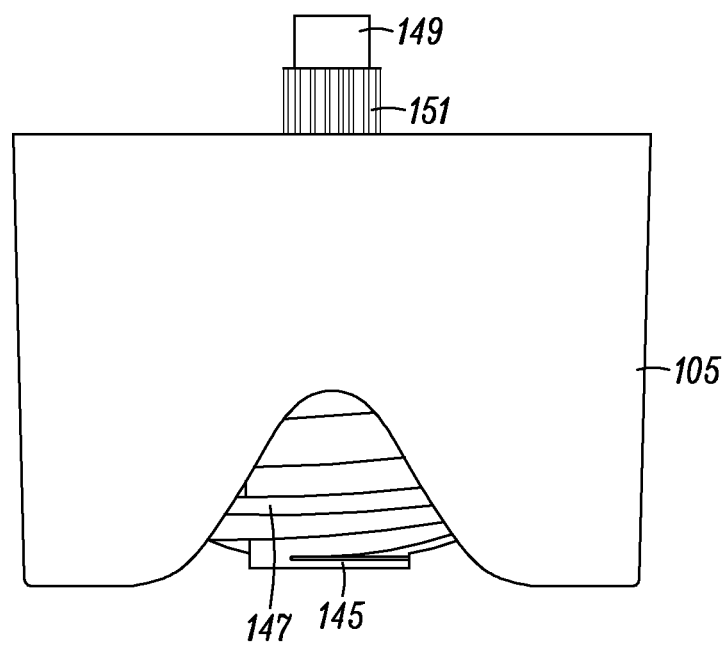
FIGS. 16A-B are side and perspective views of the of the lower portion of the housing of FIG. 11, showing the reset button in a default position.
Figure 16B:
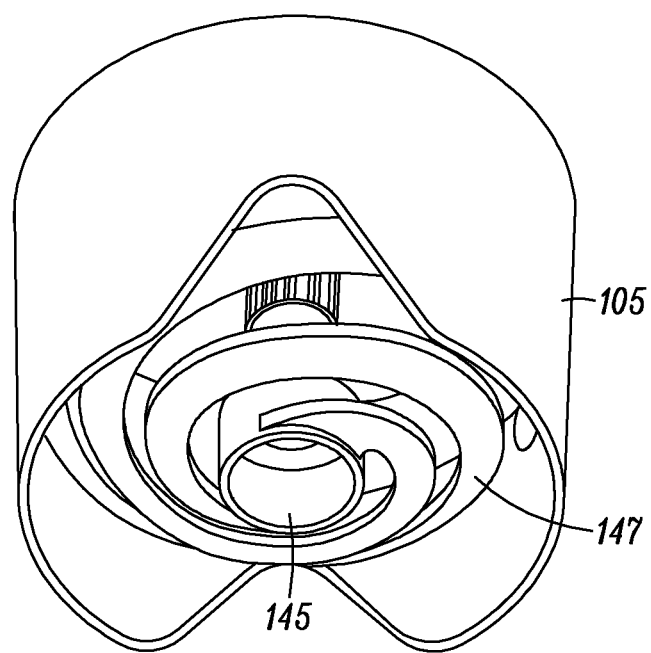
Figure 17A:
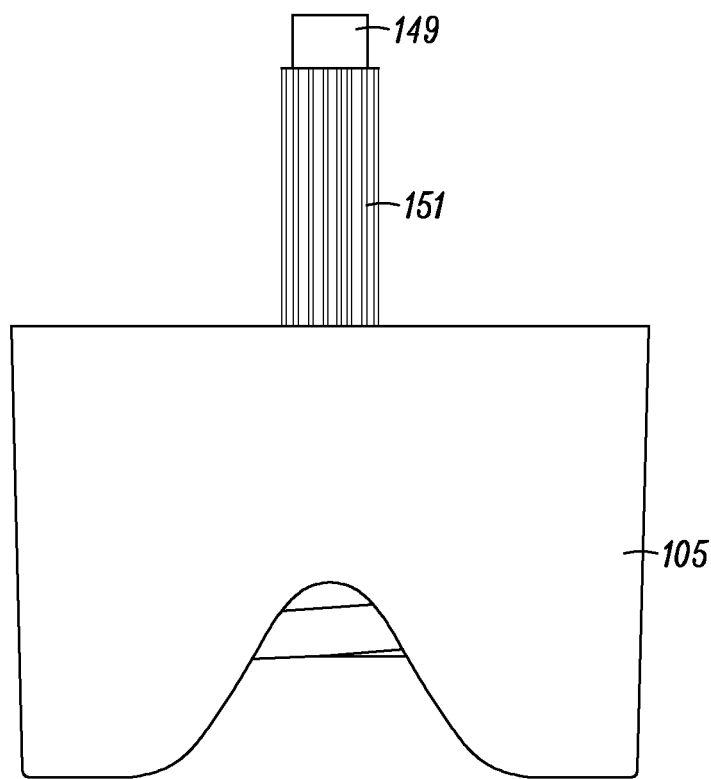
FIGS. 17A-B are side and perspective views of the of the lower portion of the housing of FIG. 11, showing the reset button in an extended position for resetting the valve of FIG. 8 to the closed position shown in FIG. 13; and, FIGS. 18A-C are bottom views of the device of FIG. 1, showing rotation of the reset button to selectively adjust the position of the valve brace relative to the valve of FIG. 8.
Figure 17B:
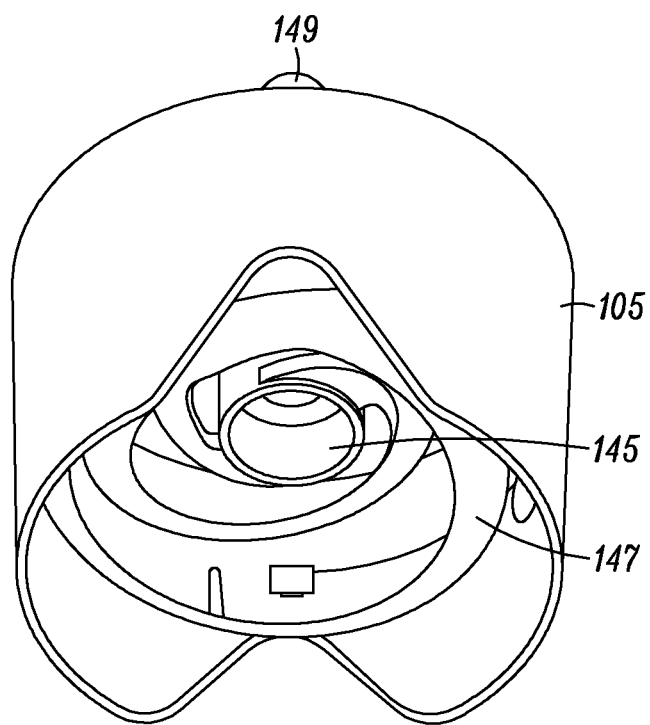

Upon completion of exhalation, the valve 109 may be reset to the closed position, shown in FIG. 13, by depressing the reset button 145, as shown in FIGS. 16A-B and 17A-B. FIGS. 16A-B show the reset button 145 and the molded-in spring 147 in a default, or "at-rest" position. In this position, the rod 149 is not in engagement with the valve 109, as seen in FIGS. 13-14. FIGS. 17A-B show the reset button 145 and the molded-in-spring 147 in a depressed position. In this position, the rod 149 is in an extended position, such that it may engage the flap 135 of the valve 109, pushing the flap 135 back through the opening 127, as shown in FIG. 15. Depression of the reset button 145 also creates a tension in the molded-in spring 147. When the reset button 145 is released in the depressed position, the tension in the molded-in spring 147 returns the reset button 145, the rod 149, and the molded-in spring 147 to the default or "at-rest" position, shown in FIGS. 16A-B, as well as FIG. 13. Similarly, pushing the flap 135 to the position shown in FIG. 14 creates a tension or a bias in the valve 109, such that when the rod 149 returns to the "at-rest" position, the flap 135 returns to the closed position, shown in FIG. 13. The aforementioned process may then be repeated by the user. A user may also inhale through the inlet or mouthpiece 115, causing the flap 135 of the valve 109 to move from the closed position, as shown in FIG. 13, to an open inhalation position, for example, as shown in FIG. 15.

Figure 18A:
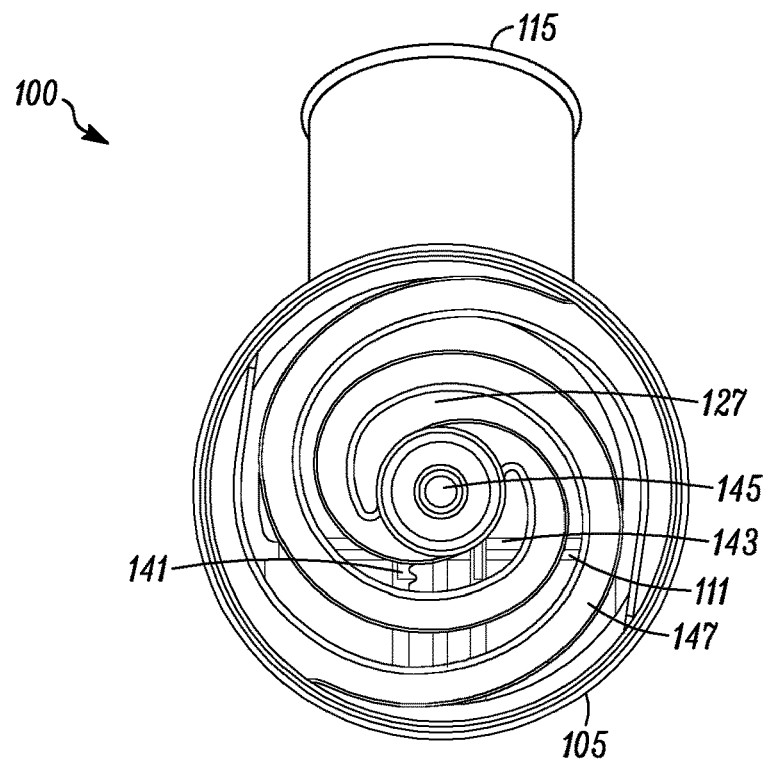
Figure 18B:
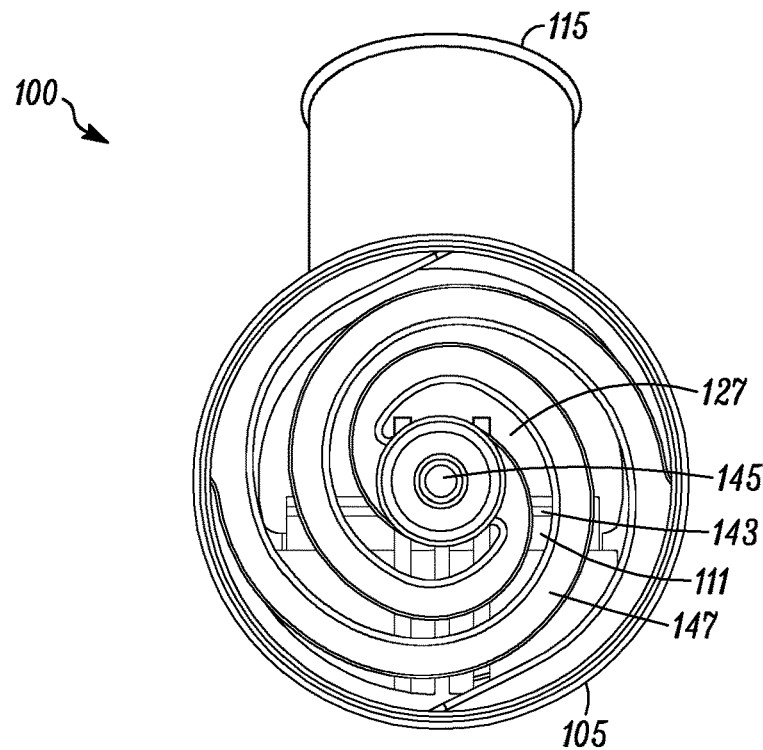
Figure 18C:
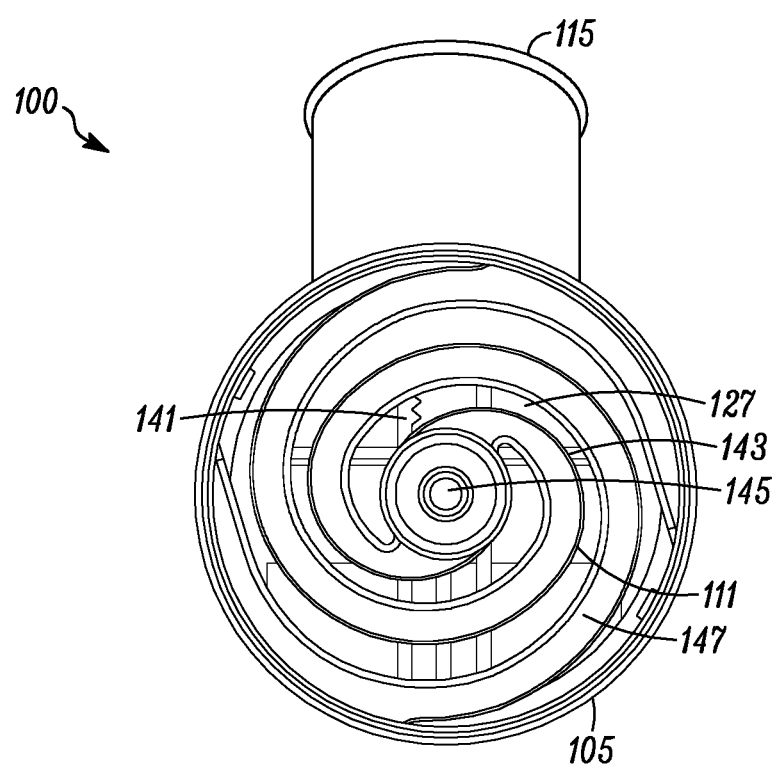

A user may selectively adjust the threshold exhalation pressure at which the valve 109 blows through the opening 127 by rotating the reset button 145, as illustrated in FIGS. 18A-C. Specifically, FIGS. 18A-C are bottom views of the device 100, illustrating rotation of the reset button 145 to selectively adjust the position of the valve brace 111 relative to the opening 127 and the valve 109. As noted above, the reset button 145 includes a rod 149 having a series of gear teeth 151 (e.g., a pinion) for engaging a corresponding series or a rack of teeth 141 on the valve brace 111. Therefore rotation of the reset button 145, and consequently the rod 149 and gear teeth 151, results in linear movement of the valve brace 111, as shown in FIGS. 18A-C. As shown in FIG. 2, a plurality of detents 104 on the middle housing portion 103 are configured to engage at least one detent 106 on the lower housing portion 105 to provide the user with tactile feedback as the user rotates the reset button 145 to adjust the threshold exhalation pressure in discrete intervals. The engagement of the at least one detent 106 with the plurality of detents 104 also operates to fix the reset button 145 to the extent the reset button 145 is rotationally biased by the molded-in spring 147 after rotation by a user.

FIG. 18A shows the valve brace 111, and therefore the support face 143, in a retracted position in which the support face 143 is not supporting the flap 135 of the valve 111, and the opening 127 remains unobstructed by the support face. FIG. 18B shows the valve brace 111 in a partially extended position in which the support face 143 is supporting a portion of the flap 135 and partially obstructing the opening 127. FIG. 18C shows the valve brace 111 in a further extended position in which the support face 143 is supporting a larger portion of the flap 135, and obstructing a larger portion of the opening 127. By rotating the reset button 145 to advance the position of the valve brace 111 relative to the opening 127 and the valve 109, the user is able to selectively increase the portion of the valve brace supporting the flap 135, and also reduce the area of the flap 135 exposed to the exhalation pressure that is subject to blow through the opening 127. Likewise, by rotating the reset button 145 in the opposite direction to retract the position of the valve brace 111 relative to the opening 127 and the valve 109, the user is able to selectively decrease the portion of the valve brace supporting the flap 135, and also increase the area of the flap 135 exposed to the exhalation pressure that is subject to blow through the opening 127. In this way, the use may selectively increase or decrease the threshold exhalation pressure.

What is claimed is:

1. A respiratory treatment device comprising:
an inlet configured to receive exhaled air into the device;
an outlet configured to permit exhaled air to exit the device;
a valve moveable in response to a threshold exhalation pressure at the inlet between a closed position where the flow of air from the inlet to the outlet is restricted, and an open exhalation position where the flow of air from the inlet to the outlet is less restricted; and,
a valve brace configured to support the valve, wherein a position of the valve brace relative to the valve is selectively adjustable to increase or decrease the threshold exhalation pressure;
wherein the valve is configured to remain in the open exhalation position during the flow of air from the inlet to the outlet; wherein the valve is a two-way flap valve.

2. The respiratory treatment device of claim 1, wherein selective adjustment of the position of the valve brace relative to the valve increases or decrease a stiffness of the valve.

3. The respiratory treatment device of claim 1, wherein selective adjustment of the position of the valve brace relative to the valve increases or decreases an area of the valve supported by the valve brace.

4. The respiratory treatment device of claim 1, further comprising a valve seat configured to retain the valve in the closed position until the threshold exhalation pressure is obtained at the inlet.

5. The respiratory treatment device of claim 1, further comprising a valve seat positioned to engage a periphery of the valve.

6. The respiratory treatment device of claim 1, further comprising a first housing component and a second housing component, wherein the first housing component and the second housing component are removably connected.

7. The respiratory treatment device of claim 1, wherein the chamber inlet comprises a mucus trap.

8. The respiratory treatment device of claim 1, wherein the inlet comprises a screen having a plurality of openings.

9. A respiratory treatment device comprising:
an inlet configured to receive exhaled air into the device;
an outlet configured to permit exhaled air to exit the device;
a valve moveable in response to a threshold exhalation pressure at the inlet between a closed position where the flow of air from the inlet to the outlet is restricted, and an open exhalation position where the flow of air from the inlet to the outlet is less restricted; and,
a valve brace configured to support the valve, wherein a position of the valve brace relative to the valve is selectively adjustable to increase or decrease the threshold exhalation pressure;
wherein the valve is moveable in response to an inhalation pressure at the inlet between the closed position and an open inhalation position where the flow of air from the outlet to the inlet is less restricted; wherein the valve is a two-way flap valve.

10. The respiratory treatment device of claim 9 wherein the valve is biased toward the closed position when the valve is moved from the closed position.

11. The respiratory treatment device of claim 9 wherein the valve is configured to remain in the open exhalation position during the flow of air from the inlet to the outlet.

12. A respiratory treatment device comprising:
an inlet configured to receive exhaled air into the device;
an outlet configured to permit exhaled air to exit the device;
a valve moveable in response to a threshold exhalation pressure at the inlet between a closed position where the flow of air from the inlet to the outlet is restricted, and an open exhalation position where the flow of air from the inlet to the outlet is less restricted;
a valve brace configured to support the valve, wherein a position of the valve brace relative to the valve is selectively adjustable to increase or decrease the threshold exhalation pressure; and,
a reset button configured to return the valve from the open exhalation position to the closed position; wherein the valve is a two-way flap valve.

13. The respiratory treatment device of claim 12, wherein the resent button is connected to the device by a molded-in spring.

14. The respiratory treatment device of claim 12, wherein the reset button is selectively rotatable to adjust the position of the valve brace relative to the valve.

15. The respiratory treatment device of claim 12, wherein the reset button comprises a plurality of gear teeth configured to engage a plurality of teeth on the valve brace.

16. The respiratory treatment device of claim 12, wherein the valve is configured to remain in the open exhalation position during the flow of air from the inlet to the outlet.

* * * * *